United States Patent
Amanullah et al.

(10) Patent No.: US 7,768,633 B2
(45) Date of Patent: Aug. 3, 2010

(54) MULTIPLE SURFACE INSPECTION SYSTEM AND METHOD

(75) Inventors: Ajharali Amanullah, Singapore (SG); Han Cheng Ge, Singapore (SG); Huek Choy Tan, Singapore (SG); Hing Tim Lai, Singapore (SG)

(73) Assignee: ASTI Holdings Limited, Singapore (SG)

( * ) Notice: Subject to any disclaimer, the term of this patent is extended or adjusted under 35 U.S.C. 154(b) by 502 days.

(21) Appl. No.: 11/732,888

(22) Filed: Apr. 5, 2007

(65) Prior Publication Data

US 2008/0246958 A1 Oct. 9, 2008

(51) Int. Cl.
*G01N 21/00* (2006.01)
(52) U.S. Cl. .................... 356/237.1; 356/237.6
(58) Field of Classification Search .... 356/237.1–237.6
See application file for complete search history.

(56) References Cited

U.S. PATENT DOCUMENTS

| | | | | |
|---|---|---|---|---|
| 4,701,049 A | * | 10/1987 | Beckman et al. | 356/3.07 |
| 2005/0185181 A1 | | 8/2005 | Salvi | |
| 2006/0142971 A1 | * | 6/2006 | Reich et al. | 702/150 |

* cited by examiner

*Primary Examiner*—Gregory J Toatley, Jr.
*Assistant Examiner*—Iyabo S Alli
(74) *Attorney, Agent, or Firm*—Jackson Walker L.L.P.; Christopher J. Rourk

(57) ABSTRACT

A system for inspecting components is provided. The system includes a prism having a first end, a second end, a first reflecting surface, and a second reflecting surface. The first end of the prism is located in a plane that is parallel to and axially separated from a plane of one or more of a plurality of inspection pieces. An image data system is disposed beyond the second end of the prism and generates image data of one or more of the inspection piece that includes a top surface of at least one of the inspection pieces and at least one side of at least one of the inspection pieces. An inspection piece transportation system, such as a pick and place tool or conveyor, moves a plurality of inspection pieces past the first end of the prism through an inspection area.

20 Claims, 5 Drawing Sheets

MULTIPLE SURFACE INSPECTION SYSTEM AND METHOD

FIELD OF THE INVENTION

The invention relates to component inspection systems, and in particular to a system and method for multiple surface inspection that does not require the component being inspected to be placed within the inspection equipment.

BACKGROUND OF THE INVENTION

It is known to inspect multiple surfaces of a component using a single set of image data. However, existing methods and systems for performing such inspections require the component to be placed within the inspection apparatus, such as by lowering or raising the component into position. While some systems and methods allow some inspection processes to be performed using an inspection apparatus that is placed over or under the component being inspected, the image data from the different surfaces of such systems and methods is not in the same focal plane, and is contained within an area that significantly larger than the total surface area of the component being inspected. As such, the resolution of such systems and methods is low, or they require different image data generation systems having different focal lengths.

SUMMARY OF THE INVENTION

In accordance with the present invention, a system and method for performing multiple surface inspection of a component are provided that overcome known problems with systems and methods for performing multiple surface inspection of components.

In particular, a system and method for performing multiple surface inspection of components are provided that provide high resolution and allow a single set of image data to be generated containing image data from each surface without the need to compensate for different focal lengths.

In accordance with an exemplary embodiment of the present invention, a system for inspecting components is provided. The system includes a prism having a first end, a second end, a first reflecting surface, and a second reflecting surface. The first end of the prism is located in a plane that is parallel to and axially separated from a plane of one or more of a plurality of inspection pieces. An image data system is disposed beyond the second end of the prism and generates image data of one or more of the inspection piece that includes a top surface of at least one of the inspection pieces and at least one side of at least one of the inspection pieces. An inspection piece transportation system, such as a pick and place tool or conveyor, moves a plurality of inspection pieces past the first end of the prism through an inspection area.

The present invention provides many important technical advantages. One important technical advantage of the present invention is an inspection system that utilizes prisms with two reflecting surfaces that compensate for the focal length difference between the different inspection surfaces and which allow the inspection surfaces to be placed in close proximity with each other, so as to increase the resolution of the image data.

Those skilled in the art will further appreciate the advantages and superior features of the invention together with other important aspects thereof on reading the detailed description that follows in conjunction with the drawings.

DETAILED DESCRIPTION OF PREFERRED EMBODIMENTS

Figure 1:
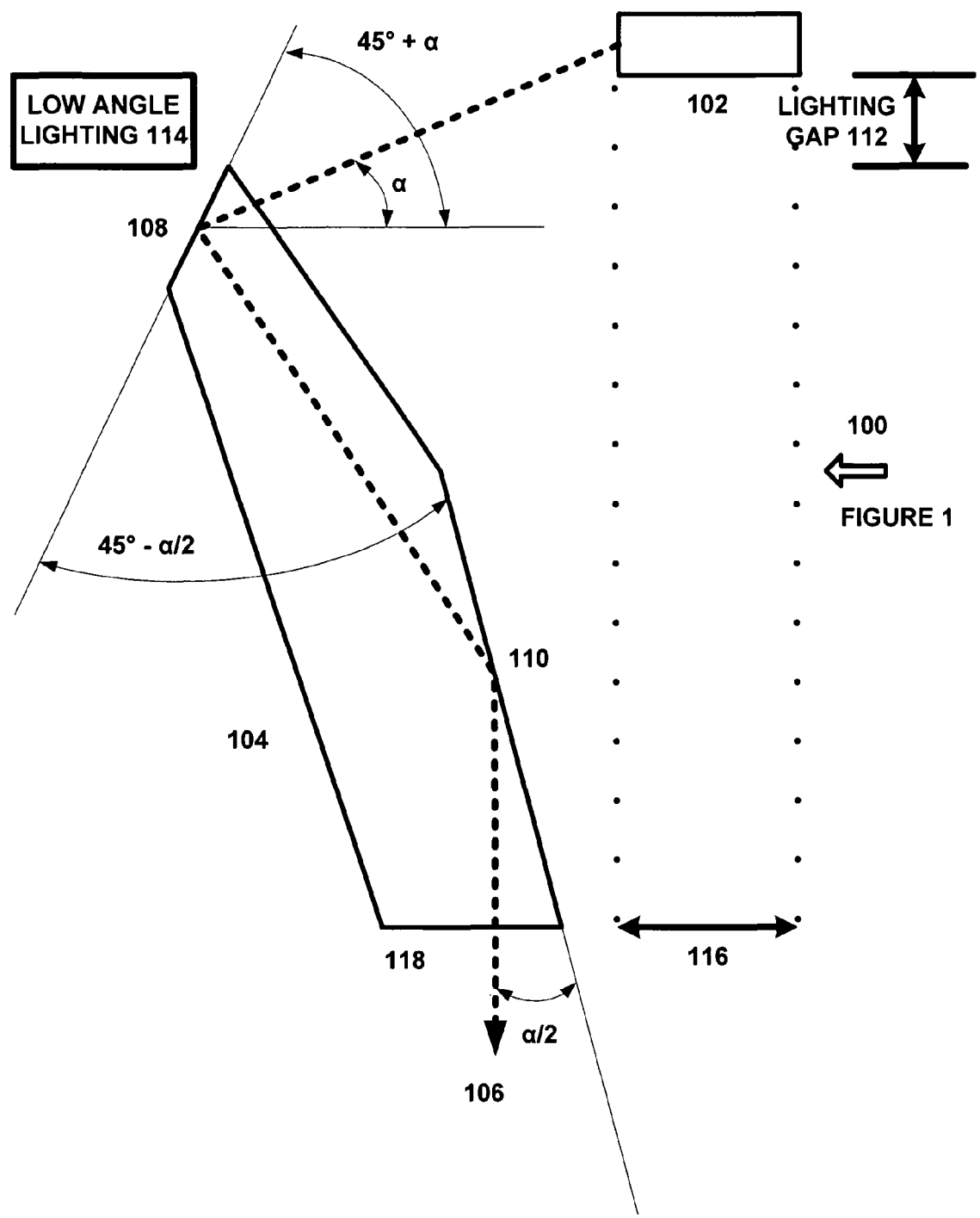
FIG. 1 is a diagram of a system for inspecting objects in accordance with an exemplary embodiment of the present invention.

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

FIG. 1 is a diagram of a system 100 for inspecting objects in accordance with an exemplary embodiment of the present invention. System 100 allows the top and sides of an object to be inspected using a single set of image data. The term "top" will be used throughout the detailed description and claims to designate the surface of the component that is directly facing the camera or other image data generation system, even though that surface might be the bottom or one of the sides of the component as it is ultimately used.

System 100 includes inspection piece 102 and prism 104. Prism 104 is configured so as to reflect light on the path shown by dashed line 106, such that the side of inspection piece 102 can be seen from the bottom face 118 of prism 104. In this manner, the camera or other device generating image data can generate image data of the top of inspection piece 102 as well as the side of inspection piece 102 as seen from the bottom face 118 of prism 104 in the direction indicated by the arrow of dashed line 106.

While mirrors could also be used to generate such image data, one draw back of mirrors is that the focal length of the path from the side of inspection piece 102 to a position parallel to the bottom face 118 of prism 104 will be longer than the focal length of the path from the top of inspection piece 102 to the viewing frame 116 of the top of inspection piece 102 that is also parallel to bottom face 118 of prism 104. Because prism 104 can be used to adjust the focal length so as to match the focal length of the direct image from the surface of inspection piece 102 to viewing frame 116, the effective focal length for the side image as seen at the bottom face 118 of prism 104 and the top of inspection piece 102 to viewing frame 116 can be the same, thus allowing a single set of image data to be readily generated for use in inspecting inspection piece 102.

In addition, if a mirror was used to generate an image of the sides of inspection piece 102, the field of view would be larger. In that embodiment, a large number of pixels of image data would need to be generated for the space between the top of inspection piece 102 and the image available from a mirror showing the side of inspection piece 102. System 100 thus allows a higher pixel density image to be formed that includes the image data from the top of inspection piece 102 in viewing frame 116 and the side of inspection piece 102 through bottom face 118 of prism 104.

As shown in FIG. 1, the angle α defines the relationship between the reflecting surfaces 108 and 110 of prism 104. The angle α is measured between the plane parallel to the point of reflection at first reflecting surface 108 and the plane of the inspection piece 102, at the point of reflection. The angular relationship between the plane of first reflecting surface 108 and the plane parallel to the plane of the inspection piece 102 at the point of reflection is 45°+α, and the angular relationship between first reflecting surface 108 and second reflecting surface 110 is 45°−α/2, such that the typical range for is α is 20° to 50°. In addition, it can be seen that there is a lighting gap 112 between the plane containing the top of prism 104 and the plane containing the top of inspection piece 102. Lighting gap 112 needs to be large enough to allow a low angle lighting source 114 to illuminate the top and sides of inspection piece 102. As such, the use of prism 104 provides the additional advantage of increasing lighting gap 112 over that of prior art systems.

Figure 2:
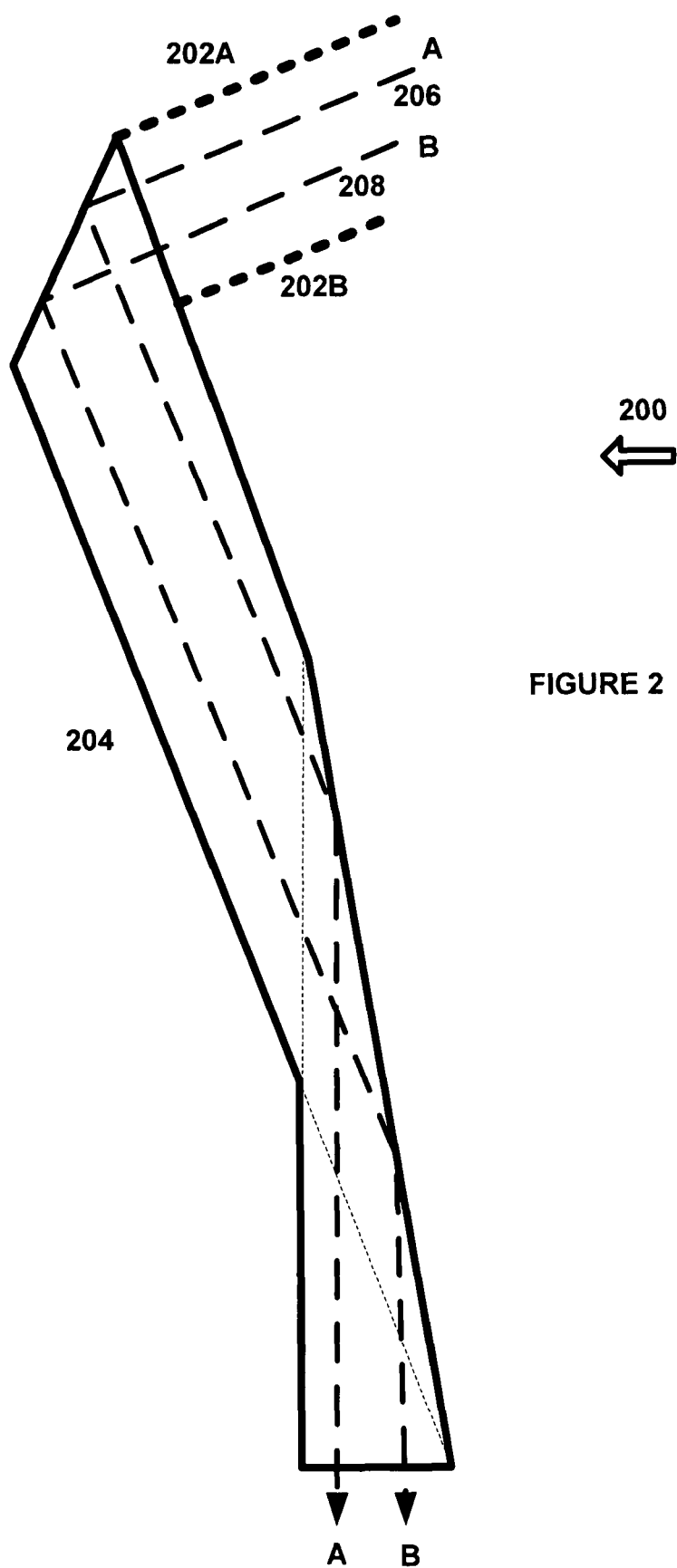
FIG. 2 is a diagram of a prism in accordance with an exemplary embodiment of the present invention.

FIG. 2 is a diagram of a prism 200 in accordance with an exemplary embodiment of the present invention. Unlike prism 104 which is a five sided prism having three obtuse angles and two acute angles, prism 200 is a six sided prism having three obtuse angles, one right angle, and two acute angles. Prism 200 includes a field of view identified by lines 202A and 202B. As shown in FIG. 2, the points A and B along the sides of an inspection object would be reflected through prism 204 along the dashed lines shown as 206 and 208. The resultant image at the bottom of prism 204 would invert the position of the points A and B, such that point A would be on the left side of point B. As such, the apparent position of the sides of the inspection item would be opposite that of the apparent position of the sides of the inspection as viewed by a single mirror. Likewise, dashed lines are shown within prism 204 that indicate the relative position of the various sides of prism 204. The angular relationships between the reflecting surfaces of prism 204 are similar to those shown in FIG. 1.

In operation, prism 204 can be used to generate the image of a side of an inspection object, so as to allow the top and sides of an inspection object to be captured in a single set of image data. Because the focal length of the path from the sides of the image object through the prism 204 can be adjusted to match the focal length of the path from the top of an object under inspection directly to the image data generation system, it is possible to focus on both the side images and the top surface image of the inspection item using a single image data generation system, such as a digital imaging system.

Figure 3:
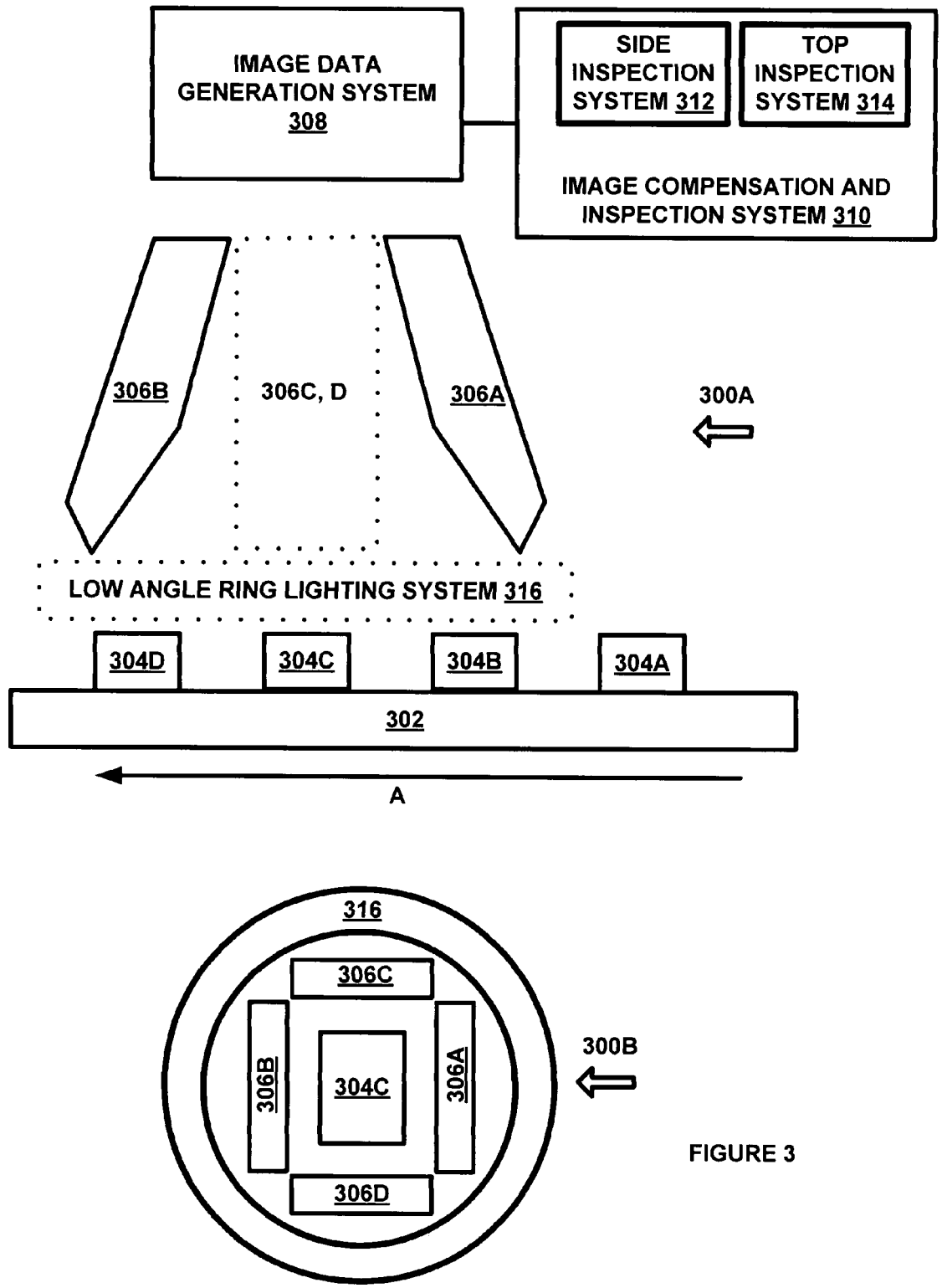
FIG. 3 is a diagram of a system for inspecting components in accordance with the exemplary embodiment of the current invention.

FIG. 3 is a diagram of a system 300 for inspecting components in accordance with an exemplary embodiment of the present invention. System 300 includes views 300A and 300B. In view 300A, an inspection piece transportation system such as conveyor 302 moving in the direction shown by arrow A carries inspection pieces 304A through 304D past an inspection area. Prisms 306A through 306D capture image data from the sides of inspection pieces 304A through 304D. Image data generation system 308 is positioned over the viewing area formed by the top surfaces of prisms 306A through 306D and the viewing area directly over inspection pieces 304A through 304D as they move under image data generation system 308.

As previously noted, prisms 306A through 306D have a focal length that is equal to the focal length through air from the surface of inspection pieces 304A through 304D as they pass through the viewing area of image data generation system 308. In this manner, image data generation system 308 can generate a set of image data that contains the top of inspection pieces 304A through 304D as well as the sides. Low angle ring lighting system 316 provides lighting to the components under inspection in manner that does not over-illuminate either the sides or the top surface of a given component, such as by use of rows of light-emitting diodes set to different brightness values or in other suitable manners.

Image compensation and inspection system 310 is coupled to image data generation system 308. As used herein, the term "coupled" and its cognate terms such as "couples" or "couple," can include a physical connection (such as a wire, optical fiber, or a telecommunications medium), a virtual connection (such as through randomly assigned memory locations of a data memory device or a hypertext transfer protocol (HTTP) link), a logical connection (such as through one or more semiconductor devices in an integrated circuit), or other suitable connections. In one exemplary embodiment, a communications medium can be a network or other suitable communications media.

Image compensation and inspection system 310 includes side inspection system 312 and top inspection system 314, each of which can be implemented in hardware, software, or a suitable combination of hardware and software, and which can be one or more software systems operating on a general purpose processing platform. As used herein, a hardware system can include a combination of discrete components, an integrated circuit, an application-specific integrated circuit, a field programmable gate array, or other suitable hardware. A software system can include one or more objects, agents, threads, lines of code, subroutines, separate software applications, two or more lines of code or other suitable software structures operating in two or more software applications or on two or more processors, or other suitable software structures. In one exemplary embodiment, a software system can include one or more lines of code or other suitable software structures operating in a general purpose software application, such as an operating system, and one or more lines of code or other suitable software structures operating in a specific purpose software application.

Image compensation and inspection system 310 receives image from image data generation system 308 and provides the side image data to side inspection system 312 and the top image data to top inspection system 314. In one exemplary embodiment, image compensation and inspection system 310 can locate areas having image data of one of inspection pieces 304A through 304D, such as by using predetermined templates, image detection techniques or other suitable processes. As shown in 300B, the exemplary set of image data generated by image data generation system 308 can include a top of inspection piece 304C as well as the sides of inspection piece 304C as seen through prisms 306A through 306D. Image compensation and inspection system 310 isolates the images from the sides of inspection piece 304 using prisms 306A through 306D and provides them to side inspection system 312 for analysis, such as by directly transferring pixels, by compensating the image for any distortion generated by the prism associated with the image, or in other suitable manners. Likewise, the top of the inspection piece 304C is provided to top inspection system 314. In this manner, the top and sides of an item under inspection can be generated where the focal length of the path of viewing from image data generation system 308 to the inspection piece 304A through 304D that is being inspected is the same as the sides view. Likewise, top inspection system 314 allows image data for the top of inspection piece 304C to be generated and inspected, such as using pattern matching, location of image data from predetermined areas, masking, pixel histogram data, or other suitable data.

Figure 4:
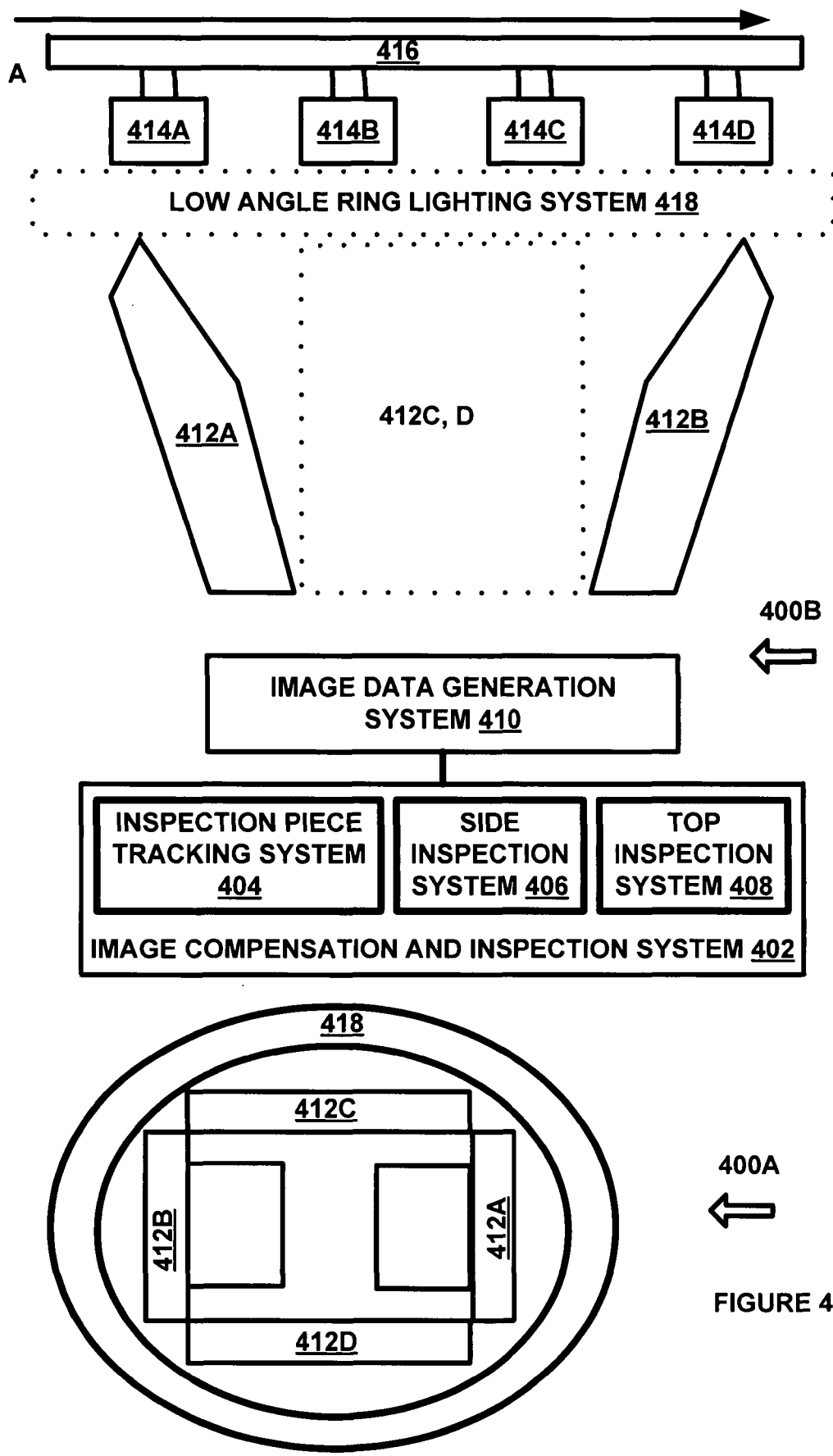
FIG. 4 is a diagram of an inspection system in accordance with an exemplary embodiment of the present invention.

FIG. 4 is a diagram of an inspection system 400 in accordance with an exemplary embodiment of the present invention. Inspection system 400 is shown in views 400A and 400B. As shown in view 400B, image compensation and inspection system 402 includes inspection piece tracking system 404, side inspection system 406, and top inspection system 408. Image data generation system 410 generates image data from the field of view that encompasses a plurality of inspection pieces 414A through 414D, either by directly viewing the tops of inspection pieces such as the exemplary view of inspection pieces 414B and 414C, or by viewing the sides of inspection pieces through prisms 412A through 412D. Low angle ring lighting system 418 provides lighting to the components under inspection in manner that does not over-illuminate either the sides or the top surface of a given component, such as by use of rows of light-emitting diodes set to different brightness values or in other suitable manners.

As shown in 400A, the exemplary view generated by image data generation system 410 includes the tops of inspection pieces 414B and 414C as well as a side of inspection piece 414B, a side of each of inspection pieces 414B and 414C through prism 412C, the side of inspection piece 414C through prism 412A, and the sides of inspection pieces 414B and 414C through prism 412B. Because the image data includes different sides for multiple pieces, inspection piece tracking system 404 identifies and tracks which side image is associated with which inspection piece. In one exemplary embodiment, as inspection pieces are moved by an inspection piece transportation system such as pick and place tool 416 in the direction of arrow A, they are scanned across the field of view of image data generation system 410. Image compensation and inspection system 402 receives the image data and identifies the inspection pieces, the tops, and the sides from prisms 412A through 412D and by direct viewing from the surface of the inspection pieces. Likewise, suitable compensation processing can be performed to compensate for any image distortion introduced by translation of the side image data by the associated prism. Side inspection system 406 and top inspection system 408 are used to analyze image data to determine whether the image data indicates that the inspection piece is acceptable. Inspection piece tracking system 404 receives the side image data testing results from side inspection system 406 and the top inspection system 408 results and determines whether a complete set of all four sides and the top of an inspection piece has been generated. Image compensation and inspection system 402 generates indications of unacceptable pieces, such that pieces can be rejected. In one exemplary embodiment, pick and place tool 416 can be controlled so as to release an item that has failed inspection in a predetermined location, an operator notification can be generated so as allow the piece to be manually inspected, or other suitable processes can be used.

Figure 5:
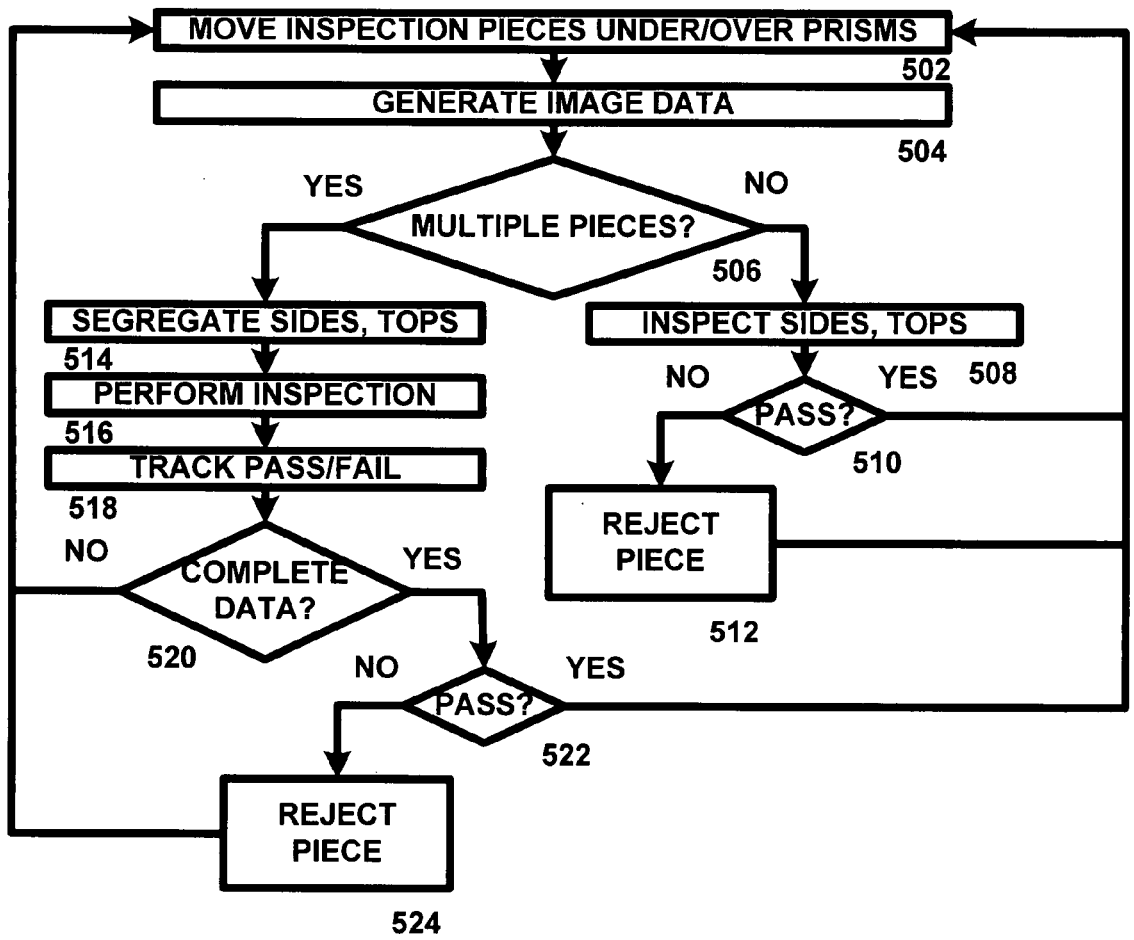
FIG. 5 is a flow chart of a method for inspecting items utilizing a prism inspection system that eliminates the need for the axial movement of inspection pieces in accordance with an exemplary embodiment of the present invention.

FIG. 5 is a flow chart of a method 500 for inspecting items utilizing a prism inspection system that eliminates the need for movement of inspection pieces in three axes in accordance with an exemplary embodiment of the present invention. Method 500 begins at 502 where inspection pieces are moved either over a plurality of prisms, under the plurality of prisms, or in other suitable manners, depending on whether the inspection pieces are being moved by a pick and place tool, a conveyer, or in other suitable manners. The method then proceeds to 504 where image data is generated. In one exemplary embodiment, the image data can be from a field view that encompasses a set of four prisms and a direct viewing area or other suitable fields of view. The method then proceeds to 506.

At 506 it is determined whether there are multiple pieces being inspected in the field of view. If it is determined that multiple pieces are not being inspected, the method proceeds to 508 where image data of the sides and tops of the inspection piece is generated and one or more image data analysis processes are performed. In one exemplary embodiment, the image data of the sides and tops can be analyzed to determine if the image data contains any indications of defects, histogram data of pixels can be generated, data from predetermined locations within the set of image data can be analyzed, or other suitable processes can be performed. The method then proceeds to 510.

At 510 it is determined whether the piece has passed inspection. If the piece has not passed inspection, the method proceeds to 512 where the piece is rejected. In one exemplary embodiment, a command can be provided to a pick and place control device to drop the piece into a defect pile, an indication can be generated for an operator to remove the piece and perform manual inspection, or other suitable processes can be used. Likewise, if it is determined at 510 that the piece has passed inspection, the method returns to 502.

If it is determined at 506 that multiple pieces are being inspected, the method proceeds to 514. At 514, image data is generated for the tops and sides of the multiple inspection pieces, and the top and side images are segregated. In one exemplary embodiment, if multiple top images and side images are present, it may be necessary to not only separate the top image data from the side image data, but also to associate the side image data with the proper top image data, so as to form a complete set of side and top image data for an inspection piece. The method then proceeds to 516 where inspection of the image data is performed. In one exemplary embodiment, the top and side image data set can be inspected using common inspection processes such as histogram inspections, inspections of pre-determined areas, or other suitable data. The method then proceeds to 518 where pass or fail results are tracked. In one exemplary embodiment, a plurality of pieces may be inspected at one time such that any defective side should be associated with one of the plurality of inspection pieces. In this exemplary embodiment, the tracking of the pass and fail results allows a complete set of image data to be generated for each inspection piece as it is moved past the inspection device, thereby allowing on the fly inspection of inspection pieces as they are being moved laterally from one location to a second location without movement of the inspection pieces in a third axis direction relative to the direction of movement, such as into the inspection device. The method then proceeds to 520.

At 520 it is determined whether a complete set of inspection data has been received for an inspection piece. If a complete set of data has not been received, the method returns to 502 and the inspection pieces are moved until a complete set of image data is generated. Otherwise, the method proceeds to 522 where it is determined whether the inspection piece has passed. If the inspection piece has passed, the method returns to 502. Otherwise, the method proceeds to 524 where the inspection piece that has failed is rejected, and a suitable process is performed or indication is generated. The method then returns to 502.

In operation, method 500 allows inspection pieces to be inspected as they are moved through a field of view of an inspection device. Unlike prior art systems that require inspection items to be moved in an axial direction so as to place the sides within the field of view of the inspection device, method 500 can be utilized by an inspection device that obtains side and top image data in a single field of view, so as to allow for continuous movement, on the fly inspection, and other suitable processes to be performed.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A system for inspecting components comprising:
   a prism have a first end, a second end, a first reflecting surface, and a second reflecting surface, the first end of the prism located in a plane that is parallel to and axially separated from a plane of one or more of a plurality of inspection pieces;
   an image data system disposed beyond the second end of the prism and generating image data of one or more of the inspection piece that includes a top surface of at least one of the inspection pieces and at least one side of at least one of the inspection pieces; and
   an inspection piece transportation system moving a plurality of inspection pieces past the first end of the prism through an inspection area.

2. The system of claim 1 wherein the prism compensates a focal length of one or more sides of one or more of the inspection pieces to match a focal length of one or more top surfaces of one or more of the inspection pieces.

3. The system of claim 1 further comprising an image compensation and inspection system receiving the image data from the image data system and separating image data of the top surface of at least one of the inspection pieces from image data of the side of at least one of the inspection pieces.

4. The system of claim 3 wherein the image compensation and inspection system further comprises a side inspection system receiving the image data of the side of at least one of the inspection pieces and generating pass/fail data.

5. The system of claim 3 wherein the image compensation and inspection system further comprises a top inspection system receiving the image data of the top of at least one of the inspection pieces and generating pass/fail data.

6. The system of claim 1 further comprising an image compensation and inspection system receiving the image data from the image data system and separating image data of the top surface of two or more of the inspection pieces from image data of the sides of two or more of the inspection pieces.

7. The system of claim 6 wherein the image compensation and inspection system further comprises an image piece tracking system associating the image data of the top surface of each of the two or more inspection pieces with the corresponding image data from the side of each of the two or more inspection piece for each inspection piece.

8. The system of claim 1 wherein the first reflecting surface of the prism and the second reflecting surface of the prism are separated by an angle 45°-α/2, wherein α is an angle between a plane, at a point of reflection of the first reflecting surface of the prism that is parallel to the plane of one or more of a plurality of inspection pieces, and a point on the side of one or more of the plurality of inspection pieces, and where a is between 20° and 50°.

9. The system of claim 1 wherein low angle lighting is provided in a gap between the plane that is parallel to and axially separated from the plane of one or more of the plurality of inspection pieces and a second plane that is parallel to the topmost surface of one or more of the plurality of inspection pieces.

10. A method for inspecting components comprising:
    moving inspection pieces through an inspection area that is outside of a first end of a plurality of prisms, each of the prisms having at least two reflecting surfaces;
    generating one set of image data at a second end of the plurality of prisms, the one set of image data including a plurality of sides and a top surface of one or more inspection pieces; and
    performing image data analysis of the image data of each of the plurality of sides and of the image data of the top surface of the one or more inspection pieces.

11. The method of claim 10 wherein performing the image data analysis of the image data of each of the plurality of sides and of the image data of the top surface of the one or more inspection pieces comprises performing the image data analysis of the image data of each of the plurality of sides and of the image data of the top surface of two more of the inspection pieces.

12. The method of claim 11 wherein performing the image data analysis of the image data of each of the plurality of sides and of the image data or the top surface of the two more of the inspection pieces comprises segregating the side image data of one of the two or more inspection pieces from the side image data of the others of the two or more inspection pieces.

13. The method of claim 11 wherein performing the image data analysis of the image data of each of the plurality of sides and of the image data of the top surface of the two more of the inspection pieces comprises segregating the top image data of one of the two or more inspection pieces from the top image data of the others of the two or more inspection pieces.

14. The method of claim 11 wherein performing the image data analysis of the image data of each of the plurality of sides and of the image data of the top surface of the two more of the inspection pieces comprises tracking over time whether pass/fail data has been generated for each of the plurality of sides and the top surface of each of the two or more inspection pieces.

15. The method of claim 10 wherein generating the image data at the second end of the plurality of prisms of the plurality of sides and the top surface of one or more inspection pieces is performed using a single focal length for the image data of each of the plurality of sides and the image data for the top surface.

16. A system for inspecting components comprising:
    prism means for generating a side image of an inspection piece;
    means disposed beyond the prism means for generating image data of one or more inspection pieces that includes a top surface of at least one of the inspection pieces and at least one side of at least one of the inspection pieces; and
    an inspection piece transportation system moving a plurality of inspection pieces past the top surface of the prism through an inspection area.

17. The system of claim 16 wherein the prism means comprises means for compensating a focal length of one or more sides of one or more of the inspection pieces to match a focal length of one or more top surfaces of one or more of the inspection pieces.

18. The system of claim 16 further comprising means for receiving the image data and separating image data of the top surface of at least one of the inspection pieces from image data of the side of at least one of the inspection pieces.

19. The system of claim 16 further means for receiving the image data from the image data system and separating image data of the top surface of two or more of the inspection pieces from image data of the sides of two or more of the inspection pieces.

20. The system of claim 16 further comprising means for illuminating the one or more inspection pieces.

* * * * *

UNITED STATES PATENT AND TRADEMARK OFFICE
CERTIFICATE OF CORRECTION

PATENT NO. : 7,768,633 B2
APPLICATION NO. : 11/732888
DATED : August 3, 2010
INVENTOR(S) : Ajharali Amanullah et al.

Page 1 of 1

It is certified that error appears in the above-identified patent and that said Letters Patent is hereby corrected as shown below:

Col. 7, line 56, please change "piece" to -- pieces --;

Col. 7, line 59, please change "-α/2" to -- - α/2 --;

Col. 7, line 63, please change "where a is" to -- where α is --; and

Col. 8, line 26, please change "or" to -- of --.

Signed and Sealed this
Eighth Day of March, 2011

David J. Kappos
*Director of the United States Patent and Trademark Office*